United States Patent
Paschedag

[11] 3,994,603
[45] Nov. 30, 1976

[54] DETECTION SYSTEM TO DETERMINE THE TRANSMISSIVITY OF A MEDIUM WITH RESPECT TO RADIATION, PARTICULARLY THE LIGHT TRANSMISSIVITY OF SMOKE-CONTAMINATED AIR, FOR FIRE DETECTION

[75] Inventor: Hansjoachim Paschedag, Maennedorf, Switzerland

[73] Assignee: Cerberus AG, Maennedorf, Switzerland

[22] Filed: Feb. 14, 1975

[21] Appl. No.: 549,897

[30] Foreign Application Priority Data
Mar. 8, 1974   Switzerland............... 3284/74

[52] U.S. Cl. .................... 356/205; 250/575; 340/237 S; 356/206; 356/207; 356/208
[51] Int. Cl.² ............... G01N 21/22; G01N 21/12; G01N 21/26
[58] Field of Search ............ 356/72, 204, 205, 206, 356/207, 208; 340/237 S; 250/574, 575, 578

[56] References Cited
UNITED STATES PATENTS

| | | |
|---|---|---|
| 3,566,385 | 2/1971 | Lawson .......................... 356/207 |
| 3,872,315 | 3/1975 | Boll ............................... 356/207 |
| 3,880,526 | 4/1975 | Kobayashi et al. ............ 356/204 |

Primary Examiner—Vincent P. McGraw
Attorney, Agent, or Firm—Flynn & Frishauf

[57] ABSTRACT

To eliminate sources of error in fire detection apparatus regarding variation of light output from a radiation cell, and to eliminate varying ambient conditions such as dust and dirt contamination of reflectors and transducers, the radiation is directed over at least two paths by reflectors which are located such that the numbers of reflections in the paths and the reflection points are the same, whereas the lengths of the paths are different, and evaluating the difference signal to obtain a measure of the density of the medium through which the paths extend, typically the transmissivity of air which may be contaminated by smoke. In one embodiment, reflectors are located in the corners of a polygon, one of the paths extending across the polygon, and the other path extending essentially circumferentially thereof.

20 Claims, 10 Drawing Figures

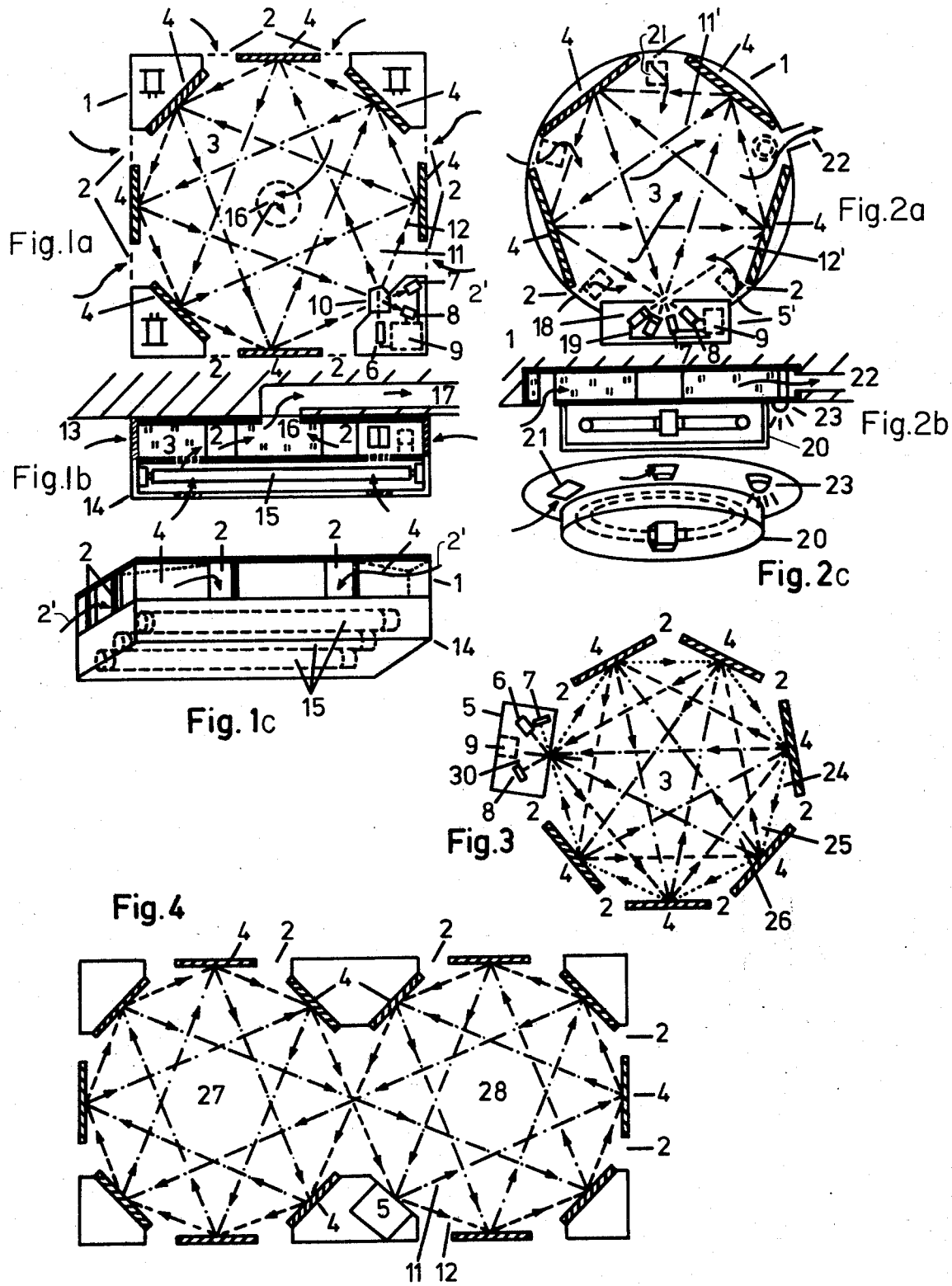

DETECTION SYSTEM TO DETERMINE THE TRANSMISSIVITY OF A MEDIUM WITH RESPECT TO RADIATION, PARTICULARLY THE LIGHT TRANSMISSIVITY OF SMOKE-CONTAMINATED AIR, FOR FIRE DETECTION

Cross reference to related patents and applications:
U.S. Pat. No. 3,316,410.
U.S. Pat No. 3,739,365.
U.S. Pat. No. 3,765,842.
U.S. Pat. application Ser. No. 416,231.
with respect to optical smoke detection circuits and systems.

The present invention relates to a system to detect the transmissivity of a medium to radiation, and more particularly to a smoke detection system in which the transmissivity of light rays through air, which may be contaminated by smoke in case of fire, is determined, to obtain an indication of a possible fire. Radiation, typically light, is directed through the medium to be examined, the light impinging on at least one photoelectric cell, or transducer, which is connected to an electrical circuit to provide an output signal, the change of which is a measure of the transmissivity of the medium.

Detectors, and systems of this type, can be used to indicate the presence of contaminants in a gaseous or fluid medium, by evaluating the attenuation of visible light, infrared light, ultraviolet radiation, or the like, which radiation is directed through the medium. The contaminants may have light dispersing effect, or light absorbing effect, due to solid particles, or aerosol components in the medium, or due to the presence of certain substances, for example certain gases in the medium, which cause a change in the transmissivity of the medium with respect to the radiation being directed therethrough. The system and detector are particularly useful as a smoke detector in fire sensing and fire alarm systems. A certain predetermined concentration of smoke particles, fire aerosols, or certain gases should be capable of being detected, so that a fire alarm signal can be given when the concentration or threshold level is exceeded. Preferably, such a smoke detector should be simple to construct, and should be unobtrusive; the smoke detector may, for example, be capable of being coupled or connected to a ventilation or light fixture normally installed in rooms or enclosed spaces which are to be supervised for the presence of smoke or fire.

The presence of suspended particles, aerosols, and the like, can be detected by determining the light dispersion thereof when light is beamed through a chamber through which the gas, typically air, is conducted; a signal is then obtained indicative of light dispersion. A photoelectric transducer is so located that, normally, it is not impinged by radiation (typically light) from a radiation source. If dispersing particles are present in the chamber, then light dispersion will result and the transducer will respond, since it will now be subjected to radiation. In another form, light is applied directly to a photosensitive element through the gaseous medium. Upon the presence of dispersing and/or of absorbing particles, the intensity of radiation is attenuated, and an output signal is derived which indicates the presence of particles in the beam of radiation due to absorption and dispersion of the direct beam. Such detectors are sometimes referred to as transmission or extinction detectors. Particle detectors, such as smoke detectors operating on the dispersion principle have the disadvantage that they are highly dependent on the optical properties of the particles. The sensitivity of such devices to detect particles having a high degree of absorption is low, and some highly absorbent particles may not be detected at all. Smoke detectors of this type respond particularly well to light colored smoke; they do not respond well to dark smoke which occurs, for example, in connection with smoky blazes. The degree of dispersion also depends highly on the size of the particles. The very small submicroscopic particles which occur in the initial stage of a fire, that is, fire aerosols, can hardly be detected or, if so, require a good deal of apparatus or special measures, for example use of very short-wave, ultraviolet radiation.

Smoke detectors operating on the transmission principle do not have the difficulties referred to; they do require, however, relatively long radiation paths in order to provide sufficient sensitivity. These paths may extend to several meters. It has already been proposed to extend the paths, within a limited space, by using reflectors which deflect the beam of radiation; multiple reflection using facing mirrors has been used. The radiation between the reflectors is attenuated by absorbent particles in the atmosphere or the medium between the reflectors. Additionally, however, and this is a disadvantage of this system, radiation between the reflectors is further attenuated by decrease in the reflecting properties of the reflectors, or the mirrors themselves. When used in smoke detectors, dirt and aging of the reflecting surfaces additionally cause attenuation of the beam between the reflectors and may lead to a false signal. The influence of change in the light output of the radiation source, due to aging, voltage variations, and the like, can be eliminated by providing a second radiation path which is directed from the source over a short path to the photoelectric element, to form a reference path; variations in intensity of radiation due to effects of the radiation source thus will be compensated, since they will occur in the same sense, and simultaneously, in the measuring path and in the reference path. The apparatus previously proposed used a reference path which is very much shorter than the beam path used as the measuring path. It was, therefore, not possible to direct the reference beam over the reflectors and, therefore, a change in the degree of reflectivity of mirrors, reflectors, and the like, due to aging, dirt, dust, or other contamination, could not be compensated. Constant cleaning and adjustment of such detectors was therefore required. High maintenance costs were thus incurred when using such detectors as fire alarm systems, entirely apart from the possibility of generation of false alarm signals and low overall reliability.

It is an object of the present invention to provide a system and apparatus to sense the transmissivity of a medium, for example air, which is apt to be contaminated by smoke, so that a fire alarm sensing system and detector are provided, which are reliable over long periods of time, require little maintenance and have a high degree of detection sensitivity with respect to particles or gas components, by sensing attenuation of radiation being directed to the medium due to the presence of suspended particles or gas components.

SUBJECT MATTER OF THE PRESENT INVENTION

Briefly, a plurality of reflection points are provided, and at least two radiation paths are directed to the reflection points, in different sequence of reflection, however, with respect to the different paths or beams. Thus, the different beams are directed to the same reflection points over different paths such that the same number of reflections will result, the overall path lengths, however, of the two paths being different. Transducers such as photoelectric cells are then provided, impinged by the beams at the end of the respective paths, connected to an evaluation circuit in such a manner that attenuation of one beam, passing through one path with respect to the other beam, passing through the other path is evaluated. This attenuation may be caused by suspended particles, aerosols, gas components, or the like, in the medium through which the beams are directed.

The invention will be described by way of example with reference to the accompanying drawings, wherein:

FIG. 1a is a highly schematic top view of a smoke detector utilizing the principles of the present invention, and illustrating mirror-type reflectors located around the periphery of a polygon;

FIG. 1b is a cross-sectional view illustrating the structure of FIG. 1a, in combination with a fluorescent ceiling fixture;

FIG. 1c is a perspective, partly phantom view of the structure of FIGS. 1a and 1b;

FIG. 2a is a highly schematic top view, partly in section, similar to FIG. 1a, and showing a different mirror arrangement;

FIG. 2b is a part-phantom side view of the structure of FIG. 2a, applied to a circular fluorescent light and ventilation ceiling fixture;

FIG. 2c is a partly phantom perspective view of the structure of FIGS. 2a and 2b;

FIG. 3 is a highly schematic top view similar to FIG. 1a, illustrating yet another mirror arrangement, and the resulting paths of the light beam;

FIG. 4 is a highly schematic top view showing a smoke detector in essentially rectangular form, which could be applied to the top of an elongated fluorescent light fixture;

Figure 5:
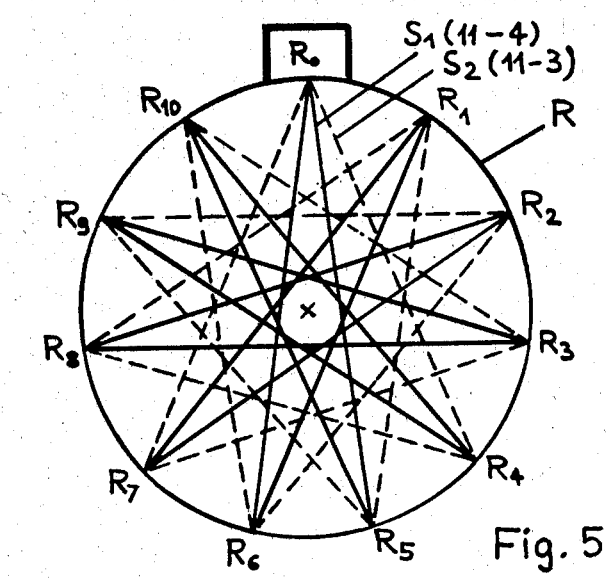
FIG. 5 is highly schematic top view illustrating the paths of beams using a curved reflecting surface which could be used, for example, in combination with the fixture illustrated in FIGS. 2b and 2c.

Referring first to FIGS. 1a to 1c, collectively referred to as FIG. 1: A housing 1 has a plurality of openings 2 at its circumference to provide for entrance of the medium to be checked or supervised, for example air which may be contaminated with smoke, and to conduct the medium into the interior of a test chamber, or measuring chamber 3. Seven mirrors 4 are located in the interior of the housing 1, having inwardly directed reflection surfaces, and being located at the sides of a regualr eight-sided polygon. The remaining side of the octagonal polygon, free from a mirror, preferably located in a corner 5 of the housing 1, is used to retain therein a radiation source 6 and two photoelectric transducers 7, 8, as well as the evaluation and operating circuit 9 therefor. These transducers may, for example, be photo cells, photo diodes, photo transistors or the like. The radiation source 6, typically a light source, is so arranged that it directs parallel beams of radiation with a suitable spectral composition towards a beam splitter 10. The light may be visible, infrared, or ultraviolet, and the source of radiation may be a laser, or any other radiation source, such as an LED source, with a suitable focusing optic. The beam splitter 10 may be a prism, such as a pentaprism (FIG. 1) or a semi-transparent mirror 30 (FIG. 3), and splits the beam derived from radiation source 6 into two beams 11, 12 which are directed into the chamber 3, at an angle with respect to each other. Beam 12, shown in broken lines, is directed to the center of the next adjacent mirror to be further reflected thereby to the center of the next immediatedly adjacent mirror and so on until beam 12 (broken line), after having been reflected seven times, is returned to the beam splitter 10. The other beam 11 — shown in chain-dotted lines — is directed from the beam splitter 10 to the third-next mirror to be reflected therefrom again to the third-next mirror, and so on, until it, likewise, after having been reflected seven times, is returned to the beam splitter 10. The two photoelectric devices 7, 8 are located in the corner 5 of the housing. These transducers are highly directional, and are so arranged that they can receive the respective beams 11, 12, without mutual interference, and provide an output signal which is truly representative of the intensity of the respective received beam only. The signals can then be evaluated, for example by forming a quotient, or a difference value. A quotient of the signals can be obtained by series-connecting the outputs of the two photo elements, so that any changes which affect the two beams, passing through the two paths, by the same factors are eliminated.

The arrangement as described directs beam 11, which may be termed the measuring beam, as well as the beam 12, which may be termed the reference beam, over the same reflection surfaces, and over the same numbers of reflection surfaces; thus, both beams are subjected to the same number of reflections, although in different sequence (with respect to the path from the source to the transducing receivers). In the arrangement described, the measuring beam 11 (chain-dotted lines) will have a path which corresponds to 7.39 times the distance of oppositely located mirror surfaces. The reference beam 12 will have a path length corresponding to 3.06 times the base path (across oppositely located mirrors). Assuming a base length of, for example, 1 m, the difference in path length between the two paths would then be 4.33 m. If the air introduced through the openings 2 into the chamber 3 contains smoke, the combination of the photoelements 7, 8 will indicate a decrease in light corresponding to the difference in path length of 4.33 m. In actual practice, and under normal conditions, this is sufficient in order to reliably and sufficiently rapidly indicate smoke formation due to a fire. The measuring beam and the reference beam are derived from the same source and are directed over the same reflection surfaces, and are subjected to the same number of reflections. Thus, any variations in the intensity of radiation and any deterioration or change in the reflectivity of the reflectors is automatically compensated. False alarms or a decrease in the sensitivity of the system is, therefore, effectively eliminated. Ingress of air into chamber 3 is schematically indicated by arrows 2'.

Disturbances derived from ambient light, room light, variations in ambient light and the like can be effectively eliminated by operating the radiation source 6 in pulses, and to provide a coincidence circuit, such as an AND-gate, for the evaluation circuitry, enabled only when a radiation pulse is emitted by the radiation source 6.

The system illustrated in FIG. 2 uses a regular pentagon, rather than an octagonal polygon, in which the reference beam 12' (dashed lines) is directed to the next adjacent mirror surface, whereas the measuring beam 11' (chain-dotted lines) is directed to the subsequent mirror surface, beyond the adjacent next one. Both beams are reflected four times, and then return to the source point. The path lengths are, respectively, 2.94 times the base distance (diameter of the circle including the polygon) for the reference beam 12' and 4.72 times the base distance for the measuring beam. Thus, assuming a base length of 1 m, the effective difference in path length will be 1.78 m, which is available for differential evaluation of the output signal. In contrast to the example illustrated in FIG. 1, where a single radiation source is used, two synchronized radiation sources 18, 19 are provided, so directed that their radiation impinges on the next adjacent or on the subsequent mirror surface. The radiation source is located in lieu of one of the mirror surfaces, in a side chamber 5'.

The number of reflection points, and the number of sides of a polygon forming reflection surfaces, respectively, is not limited to the examples shown. The following conditions must be satisfied, however: Let the number of polygonal surfaces be $p$ and the number of corners skipped be $m$: then, (a) for any given whole integer $p$, there must be at least one whole integer $m$ which is between 1 and $p/2$, and (b) $m$ and $p$ may not have a common divisor (algebraically: $1 < m < p/2$, in which $m$ and $p$ are integers and either $m/x$ or $p/x$ is not an integer). This ensures that the measuring beam will be reflected back to the origin only after $p - 1$ reflections.

FIG. 3 illustrates the paths of beams if six mirrors are used, located in form of a seven-sided polygon. Three beams 24 (dotted lines), 25 (broken lines) and 26 (chaindotted lines) are used, respectively skipping 1, 2, or 3 corners. The respective path length then will be 6.82, 5.48, and 3.04 times the diamter of the circle including the polygon.

Various other combinations of lateral sides and numbers of corners being skipped are possible; for example: 5 - 2, 7 - 2, 7 - 3, 8 - 3, or for example: 9 - 2, 9 - 4, 10 - 3, 11 - 2, 11 - 3, 11 - 4, 11 - 5, etc.

The arrangement of the paths of the beams in accordance with FIG. 2 illustrates reflection in multiple polygonal form. Complicated arrangements are possible, and matching the shape of the smoke detection chamber to a desired shape or design, for example to fit the outline of a light fixture, a ventilator, or the like. FIG. 4 illustrates thirteen reflectors, located at the lateral sides of two fitting octagons 27, 28. The result is a detection system having overall rectangualr outline with a relationship of length vs. width of 2 : 1. Many different possible paths of radiation can be derived. Generally, they must satisfy the requirement that the reference beam path and the measuring beam path are directed to the same reflectors, or reflection points, and are subjected to the same number of reflections. The sequence of reflection and the path length of the two beams must be different. It is not necessary to locate the radiation source and the radiation receivers at the same general location; they may be located at different points, as desired, and as convenient in the light of the structure to be made.

The detectors can be matched to fixtures and fittings of various types. Particles, gases, and the like, in ambient air to be supervised can be applied to the measuring chamber 3 by natural convection or by forced draft. When used as a smoke detector for fire alarms, detectors of this type are preferably located in advance of the suction opening of a ventilation system, or close to a central point in a ventilation system itself. Thus, air which is to be supervised for smoke is continuously passed through the measuring chamber. The detector can readily be combined with illumination fittings and fixtures customarily secured to the ceiling of a room, or other installation. Combined light fixtures and ventilation devices are frequently used in airconditioned rooms, the ventilation device constantly having a stream of air from the room passing therethrough. Referring to the example generally shown in FIG. 1: A ceiling 13 (FIG. 1b) has a measuring chamber 3 secured thereto; the light fixture portion 14 is located beneath the measuring chamber carrying, for example, a plurality of longitudinal fluorescent lamps 15. The suction opening 16 of a ventilation line 17 is located centrally with respect to the chamber 3 (see FIG. 1a, 1b). Ambient air is constantly sucked into the chamber 3 through the openings 2, and removed from the central opening 16 by the ventilation duct 17. Any contaminants in the air due to fire will be quickly conducted into the measuring chamber 3, where the presence of smoke can be readily detected, to provide an alarm signal. A smoke detector, combined with a ventilation system of this type has the additional advantage of extremely rapid response. The combination of the smoke detector chamber with an electric light fixture has the advantage that additional electrical conduits need not be provided, for example by providing an alarm signal over the power supply network, by using carrier or remote measuring techniques, as well known. The openings 2 can be so located that the air passes through the light fixture 14 before entering the measuring chamber 3, thereby cooling the lamps 15.

The structure shown in the FIGS. 2a–2c (collectively FIG. 2) illustrate a ventilator and light fixture combination, in further combination with a smoke detector. The smoke detector is recessed. The light fixture 20, using a circular fluorescent tube, has a somewhat smaller diameter than the smoke detector portion, so that air entrance openings 21 can be located adjacent the light fixture itself, fitting against the ceiling of the room, and placed at the bottom of the chamber 3'. A ventilation line 22 is connected laterally to the chamber 3', through which ambient air from the space to be supervised, entering through openings 21 and after having passed through the chamber 3', can be drawn off. An alarm indicator 23, and connected to the evaluation circuit 9, is likewise provided in the detector-light fixture-ventilator combination, to visually indicate when a specific detector has responded, and indicated that contaminants are present in the air being drawn through the chamber 3'.

The measuring beam and the reference beam, as well as the radiation source and the receiving transducer are physically located close to each other. If the respective beam source, beam splitters, and associated equipment, as well as the reflectors, and the receiving transducers are not accurately adjusted, then the two beams may interfere with each other; for example, a portion of the reference beam may impinge on the measuring beam transducer, or vice versa. Settling of the structure to which the detector is connected may also change the paths of the beams. Mutual interference of the beams can be eliminated by giving the measuring beam and the reference beam a different spectral composition, and then tuning the receiving transducer to be selective to the respective spectral range. Dual-type photo elements having different spectral responses can be used, or filters placed in front of the receiving transducers, and likewise immediately in front of the exit openings from the radiation source, or the beam splitter 10 (FIG. 1a), respectively, to spectrally separate the beams.

The reflectors 4 described in the foregoing embodiments were plane; as illustrated in FIG. 5, curve reflectors, such as curved mirrors, may also be used. The reflection positions R1 – R10 are arranged on a cylindrical surface R in regularly spaced distances from each other. The entire cylindrical surface R may be reflectorized so as to reflect inwardly, or curved reflecting segments may be used.

A transmitting and receiving position is schematically indicated at R', from where two beams S1 (solid lines) and S2 (broken lines) are directed to respective reflection points to be then re-reflected to other reflection points, and so on, until both beams after having been reflected ten times again return to the point of origin. The arrangement of the two beam paths S1 and S2 corresponds to the polygonal pattern 11 - 4 and 11 - 3. Reflection from a cylindrical surface causes change in the angle of aperture, or the angle included between the received and reflected beams; it is therefore recommended that the beams should be as parallel as possible, as derived, for example, from a laser, so that any energy loss is eliminated which might otherwise occur upon multiple reflection from a curved surface. Laser beams have coherent lengths of several meters and have the additional advantage that a single photoelectric receiving transducer may be used, so that the detector itself may be made independent of slightly different characteristics of two separate receiving photoelectric transducers. This can be achieved, for example (see patent application Ser. No. 6,876,174 in Switzerland) by impinging both beams on the same receiving photo element and then causing interferences thereat. The lengths of the beam paths, and the intensity of the two beams, are so arranged that the received beams cancel each other due to the interference phenomena, if there is no differential attenuation of the beam intensity. If, for example, particles or other contaminants appear in the measuring chamber, then the two beams are differentially attenuated and, upon interference, a component is left which can be evaluated as a signal by the photo-sensitive element.

Figure 6:
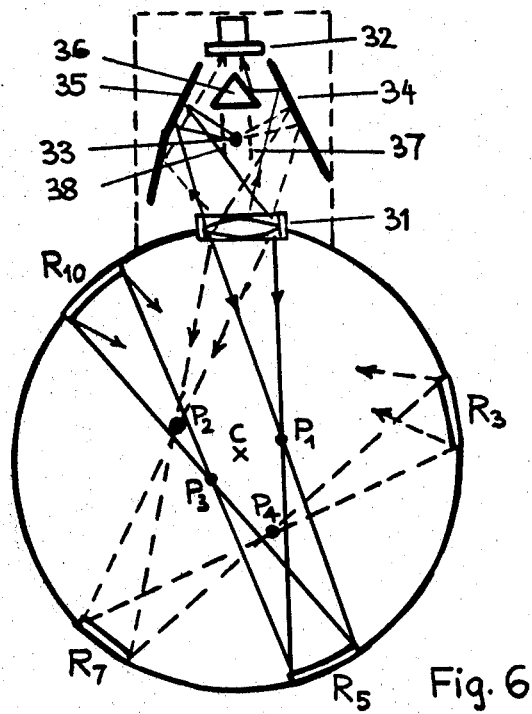
FIG. 6 is a highly schematic top view illustrating the paths of beams and using a focusing optic in combination with curved reflectors.

Energy losses due to reflection of parallel beams from an optically imaging surface, for example a cylindrical reflector, can be avoided by focusing beams by means of an optical element. FIG. 6 illustrates a lens system 31 (schematically shown as a single lens) from which beams derived from a single radiation source are focused at points P1 and P2 centrally between the reflection surfaces. These focusing points P1 and P2 are located close to the center C of the cylindrical reflector R. The radiation, therefore, upon subsequent reflection at the reflection surfaces R5 and R7, respectively, is again refocused to points P3 and P4 centrally between the reflectors and adjacent the center C of the cylinder. After multiple relfection, both beams are again applied through the optic 31 to the photoelectric receiver 32. They are again approximately focused by the optical system 31. For good efficiency of the focused beams it is desirable to use a laser beam as the source, or a point source 33, the radiation of which is directed over two mirrors 34, 35 in slightly different direction through the optical system 31. The received radiation, that is radiation returned from the measuring chamber is also directed to the mirrors 34, 35 and then to a reflecting prism 36, to be applied to a single photoelectric receiver 32. The two beams are separated from each other by devices 37, 38 in advance of the radiation source 33. These devices 37, 38 are beam modulators which differentially modulate the beams, so that the received, returned, reflected beams can be separated by demodulation of the output signal derived from the photoelectric transducer 32. Modulators 37, 38 may, for example, be cells with elecrically controlled transmissivity, such as, for example, Kerr cells, or the like.

The reflection points need not be located in the same plane. The reflection arrangements, so far described, all provided reflection points in one plane; however, three-dimensional reflection may also be used. It is necessary, as before, to provide at least two beam paths, which are directed over the same number of reflection points in different sequence and in different lengths of beam paths.

The present invention is particularly applicable for fire alarm systems. To detect fires, the wave length of radiation is preferably so selected that a spectral range is chosen in which absorption occurs due to presence of carbon monoxide (CO). Such a detector will then respond not only to smoke, but also with high sensitivity to CO traces present in the air, which traces are a reliable, unambiguous characteristic of a combustion process. The term "contaminant" used herein, therefore, is deemed to include not only solid particles, smoke and fire aerosols, but also contaminating gases which affect the medium through which the radiation is directed — typically air — to cause attenuation of the transmitted radiation.

Various changes and modifications may be made, and features described in connection with any one of the embodiments may be used with any of the others, within the scope of the inventive concept.

I claim:
1. Detection system to determine the transmissivity of a medium to radiation comprising
   a source of radiation (6, $R_o$, 33), a radiation transducer (7, 8; 32) providing an electrical output signal representative of radiation impinging thereon, means (9) providing an indication output upon change in the degree of transmissivity of the medium, and means (1, 3, 3') providing at least two paths of radiation from the source to the detector,
   comprising the improvement wherein
   said means providing said paths comprises a plurality of reflectors located to be impinged by the radiation in both said paths, said paths including said reflectors in different sequence, but with the same number of reflections, and having different total lengths between the source and the transducer so that change in the radiation transmissivity of the medium will affect attenuation of the radiation beams travelling along said respective paths differentially, due to their different lengths.

2. System to detect contaminating components in air including at least one of: gas components; aerosol particles; solid particles; smoke;
comprising the system of claim 1,
wherein the means providing an indication output are responsive to evaluated difference in attenuation of the radiation impinging on said transducer means due to said contaminating component, or components.

3. System according to claim 1, wherein the reflectors (4) are located at the sides of a regular polygon, and wherein one of the paths extends from the side of the polygon to another side of the polygon, while bypassing the same number of adjacently located sides.

4. System according to claim 1, wherein the reflectors (4) are located at the sides of a regular polygon and wherein the paths extend from one reflector to another, while bypassing the same number of corners of the polygon and wherein the number of corners being bypassed by the respective paths are different.

5. System according to claim 4, wherein the number of the polygon and the number of the corners being bypassed by both said paths of radiation do not have a common divisor.

6. System according to claim 4, wherein the polygon is an octagon, one of said beams passing over one of said paths is a measuring beam, and the other of said beams passing over the other of said paths is a reference beam;
and wherein one beam is directed to skip three corners of the octagon, and the other beam is directed to skip one corner of the octagon.

7. System according to claim 4, wherein the polygon is a pentagon, one of said beams passing over one of said paths is a measuring beam, and the other of said beams passing over the other of said paths is a reference beam;
and wherein one beam is directed to skip one corner of the pentagon, and the other beam is directed to skip two corners of the pentagon.

8. System accordng to claim 1, wherein said source of radiation (6) provides a single beam, and a beam splitter (10) is provided splitting the beam into two beams, each being directed along a respective beam path.

9. System according to claim 8, wherein the beam splitter comprises a pentaprism.

10. System according to claim 8, wherein the beam splitter comprises a semi-transparent mirror.

11. System according to claim 1, wherein the radiation transducer (7, 8) comprises a separate photoelectric transducer oriented to receive the beam from a respective path only;
and the outputs from said photoelectric transducers are connected in the circuit which forms a quotient of the respective, individual outputs.

12. System according to claim 1, wherein the radiation source (6) is a laser.

13. System according to claim 1, wherein the reflectors comprises at least a portion of a cylindrical reflection surface.

14. System according to claim 13, wherein the radiation along said paths is directed as respective parallel beams.

15. System according to claim 13, further comprising optical means (31) focusing the beams intermediate between reflectors.

16. Fire detection system to detect the presence of the results of a combustion product including at least one of: carbon monoxide; fire aerosols; smoke;
comprising the system of claim 1,
wherein the radiation source (6) directs beams of radiation through an air space which is to be supervised for the presence of the results of a combustion process, and wherein the means (9) providing an indication output are responsive to evaluate differential attenuation of radiation impinging on said transducer means and derived from respective beams passing through respective paths, said means (9) providing an alarm output when a predetermined concentration of contaminants in the air passed by said beam is sensed, as determined by a predetermined differential change in output signals from said transducers.

17. System according to claim 16, comprising a chamber (1, 3, 3'), said source of radiation directing beams of radiation through said chamber, and said reflectors (4, R) being located circumferentially about said chamber, said chamber being formed with air entry openings (2, 21) and air exit openings (16, 22) to provide for air flow through said chamber.

18. System according to claim 17, further comprising forced draft means connected to at least one of said respective openings to provide for forced draft air flow through said chamber.

19. System according to claim 17, in combination with a light fixture, said housing and chamber forming means being located above said light fixture and adapted for connection to the ceiling of a space, the air in which is to be supervised for the presence of fire-originated contaminants.

20. System according to claim 17, wherein the spectral range of radiation delivered by said source (6) is selected to have an absorption band sensitive to the presence of carbon monoxide.

* * * * *